United States Patent [19]

Fuertes et al.

[11] Patent Number: 4,845,208

[45] Date of Patent: Jul. 4, 1989

[54] PROCESS FOR THE OXIDATION OF ALDOSES, CATALYST USED IN SAID PROCESS AND PRODUCTS THUS OBTAINED

[76] Inventors: Patrick Fuertes, 207 Rue des Paris, 59000 Lille; Guy Fleche, 49 Rue G. Charlet "Le Sart", 59660 Merville, both of France

[21] Appl. No.: 7,632

[22] Filed: Jan. 28, 1987

[30] Foreign Application Priority Data

Jan. 30, 1986 [FR] France ................... 86 01306

[51] Int. Cl.$^4$ ............... C07C 59/105; C07C 51/31; C07C 51/235; B01J 23/64
[52] U.S. Cl. ................... 536/124; 536/1.1; 536/18.5
[58] Field of Search ............ 536/18.5, 18.6, 124, 536/1.1

[56] References Cited

U.S. PATENT DOCUMENTS 2,562,200  7/1951  Mehltretter ............ 536/124
2,845,439  7/1958  Reiners ................. 536/124

FOREIGN PATENT DOCUMENTS 0142725  5/1985  European Pat. Off. .

OTHER PUBLICATIONS

Kao Corp.; Chemical Abstracts, vol. 103:88175q (1985).
Kao Corp.; Chemical Abstracts, vol. 102:149721t (1985).

Primary Examiner—Ronald W. Griffin
Assistant Examiner—Nancy S. Carson
Attorney, Agent, or Firm—Larson and Taylor

[57] ABSTRACT

Process for the oxidation of aldoses and particularly of glucose into the corresponding aldonic acids, wherein oxidation is carried out in an alkaline medium by means of an oxygen-containing gas, in the presence of a catalyst obtained by adding an efficient quantity of at least one of the metals constituting the Groups IV, V and VI, or promoter, onto a catalyst consisting of palladium on an inert support.

17 Claims, No Drawings

PROCESS FOR THE OXIDATION OF ALDOSES, CATALYST USED IN SAID PROCESS AND PRODUCTS THUS OBTAINED

The present invention essentially relates to a process for the oxidation of aldoses into aldonic acids.

It is most particularly concerned with the application of the aforesaid process to the preparation of gluconic acid by oxidizing glucose.

Although, on an industrial scale, gluconic acid is at present prepared by fermentation, it has already been proposed to prepare it by chemical, electrolytic or catalytic oxidation in the presence of noble metal-containing catalysts, especially with a view to overcoming the drawbacks of the fermentation processes, particularly, in connection with the complexity of the installations necessary for the implementation thereof, with the microbiological pollution jeopardies, and with the important reaction times.

Thus, in 1947, K. HEYNS ((Annals 558, pages 187 to 192) describes the oxidation of monosaccharides and in particular of glucose by means of a catalyst obtained from the deposit of platinum on carbon, and in 1955, the UK Pat. No. 766 288 discloses the preparation of sodium gluconate by means of a catalyst obtained from the deposit of palladium on carbon.

The main barrier to the development of these catalytic oxidation processes lies in the fact that the platinum or palladium-based catalysts show a poor selectivity. Actually, the drawback of these catalysts is to simultaneously oxidize the aldehyde groups and alcohol functions, which generates in the particular case of the oxidation of glucose into gluconic acid, the occurrence of undesirable products such as glucaric acid. These reactions of uncontrolled over-oxidation are all the more pronounced since the conversion rate of glucose is high, so that it is difficult to obtain a yield of gluconic acid higher than 92-94%.

Furthermore, the palladium or platinum-based catalysts do not permit, in spite of the alkaline character of the medium within which they are used, to maintain a kinetic or speed during the reaction of oxidation which is sufficiently high to avoid the isomerization of glucose into fructose and in fact the subsequent oxidation of the fructose into 2-keto-gluconic acid.

With a view to improving the selectivity and rate of these reactions of oxidation, it has been proposed (Japanese patent No. JP 59-205 343) to constitute the catalysts to be implemented by a previous impregnation with a lead salt on a support made up of finely divided carbon, followed by the deposit of palladium, whereby lead can be replaced with selenium (patent JP 60-92240), or also with bismuth (patent EP 142 725).

These catalysts contribute to a certain improvement as regards the selectivity of the reaction of oxidation; however, they do not make it possible to ensure an economical production of aldonic acids displaying a constant purity, since they do not feature a sufficient stability to withstand the recycling operations, which is an essential criterion for these processes of catalytic oxidation to be economically practicable, said instability generating, in addition, a rapid decrease in the purity of the products thus obtained.

The main purpose of the invention is therefore to overcome these drawbacks and to provide a process for the preparation of aldonic acids and particularly gluconic acid which better meets the various prerequisites of the practice in comparison with those processes already available.

Now, the merit of the Applicants has been to demonstrate that in a surprising and unexpected way, an economical production of aldonic acids and especially of gluconic acid displaying a constant purity became feasible from the moment that, in a process of the type involved, there is utilized a catalyst obtained by adding an efficient amount of at least one of the metals of the group constituted by the groups IV, V and VI of the periodic system, or promoter, onto a catalyst constituted of palladium on an inert support.

Consequently, the process for the preparation of aldonic acids and in particular of gluconic acid in accordance with the invention is characterized by the fact that an aldose and particularly glucose is oxidized in an alkaline medium by means of an oxygen-containing gas in the presence of a catalyst obtained by adding an efficient amount of at least one of the metals of the group constituted by groups IV, V and VI of the periodic system, or promoter, onto a catalyst constitued by palladium on an inert support.

In addition to this process for the preparation of aldonic acids, further objects of the invention are the aforesaid catalysts in their application to said process as well as the aldonic acids obtained by carrying out the same.

The aldoses other than glucose, capable of being oxidized by the process according to this invention, are those of the group comprising erythrose, threose, ribose, arabinose, xylose, lyxose, allose, altrose, gulose, mannose, idose, galactose and talose.

These aldoses can be found in the form of crystallized or not crystallized pure compounds, or in the form of technical or industrial solutions, i.e. having a lower purity.

As example, in the case of the glucose, it is known that it can advantageously be obtained in the form of solutions by processes of enzymatic and/or acid hydrolysis. These solutions, commonly referred to as starch hydrolysates are characterized by their reducing power or DE (Dextrose-Equivalent).

The process according to the invention can be carried out on any hydrolysate whose DE is higher than 90, preferably higher than 95.

The aldonic acids, resulting from the oxidation, are polyhydroxylated carboxylic monoacids, in which the aldehyde function of the aldose is oxidized into carboxylic radicals.

The preferred "promoters" are bismuth, lead, antimony, tin or selenium; those most particularly preferred being bismuth and lead. They are preferably selected in the form of salts, in order to facilitate their solubilization in an aqueous, generally acid medium.

The supply of promoters onto the catalyst constituted by palladium on an inert support can be effected by impregnation.

To achieve this, the solution of the promoter is mixed with an aqueous suspension of the supported palladium-based catalyst; the impregnation is obtained by maintaining the mixture under stirring for a duration of at least a few seconds to several hours. This time duration directly depends on the kinetic or speed of the impregnation step. It is generally comprised between 15 minutes and 2 hours.

The thus impregnaged suspension of the supported, palladium-based catalyst is then made alkaline by adding a base such as NaOH, KOH or sodium carbonate. This operation precedes the step of reduction of the promoters which is carried out at a temperature comprised between 20° and 100° C. by means of chemical reducing agents such as formalin, sodium formate, sodium boron hydride, hypophosphorous acid, hydrozine, glucose or other reducing sugars.

The catalyst thus reduced is filtered, washed, dried or used as such.

The preferred catalysts in connection with the present invention are those obtained by depositing bismuth and/or lead onto a carbon supported, palladium-based catalyst.

The palladium content of the catalyst expressed in terms of metal is generally comprised between 1 and 10 wt % with respect to the inert support.

The efficient quantity of promoter, especially of bismuth and/or lead, expressed in terms of metal, is comprised between 1 and 300 wt % and, preferably, between 5 and 100 wt % with respect to palladium.

In order to carry out the process according to the invention:

There is introduced into a reaction vessel, equipped with a stirring device, an aqueous aldose, especially a glucose solution, or a mixture of aldoses, the concentration of aldose being preferably comprised between 5 and 60 wt %, the lower limit being only imposed by a concern for profitability of the process and the upper limit taking into account the solubility of oxygen in highly viscous media and the risk or crystallization of the salt of the aldonic acid formed during the reaction, There is dispersed into said solution the catalyst used according to the invention in a quantity such that the quantity of palladium expressed in terms of metal is comprised between 0.005 and 1% by weight and, preferably, between 0.01 and 0.4 wt % with respect to the quantity of aldose.

the reaction of oxidation is started by the simultaneous introduction of a flow of air or oxygen-containing gas and of an alkaline agent, the reaction temperature generally ranging between 20° and 90° C., preferably between 25° and 60° C., the reaction time being comprised between 30 minutes and 5 hours.

As example, it should be noted that the oxidation of glucose into sodium gluconate is preferably carried out at a concentration of the glucose solution comprised between 20 and 40 wt %.

The alkaline agent used, is selected from sodium hydroxide, potassium hydroxide, calcium hydroxide, lithium hydroxide, magnesium hydroxide, depending on the object to be reached. Thus, NaOH will be used in order to obtain the sodium salt of the aldonic acid corresponding to the aldose used; there can also be used zinc or manganese carbonate or any other zinc or manganese salt for which the corresponding hydroxides are obtained in situ by adding an alkaline agent such as sodium hydroxide or potassium hydroxide.

The alkaline agent is also intended for neutralizing the aldonic acid formed in order to maintain a constant catalytic activity during the reaction; it should enable the pH of the reaction medium to be maintained at a sufficient value in order to ensure the desorption of the aldonic acid formed and avoid the over-oxidation thereof without however causing this value to be too high, since too high a value could give rise to reactions of isomerization of aldose into ketose.

In the practice, the pH is maintained at a value comprised between 7.5 and 11.0, preferably between 8.0 and 10.0.

The process according to the invention makes it possible to obtain a conversion rate of the aldoses employed higher than 95% and more particularly comprised between 98% and 100% with a high selectivity ranging from 97 to 100%.

These remarkable performance are all the more exceptional since they are not affected by an important number of recycling operations of the catalysts implemented in accordance with the invention, which catalysts show high stability and whose life duration is markedly higher than the life of those catalysts previously used and obtained by impregnation with a promoter before depositing the noble metal, the catalysts used according to this invention being furthermore easily regenerated by depositing a new promoter charge.

The aldonic acids obtained from the process according to the invention can advantageously be used as chelating agents, as agents intended for the cleaning of glass and metal articles or items, or as additives for detergents, medecines or drugs or foodstuff additives.

In this connection, sodium gluconate is used as a fluidifying water-reducing agent, or concrete retarding admixture in the hydraulic binders.

The invention will be better understood by means of the following non-limiting examples which illustrate advantageous embodiments of the invention.

There is first described the preparation of the catalyst used according to the invention (example 1) and the preparation of the catalyst used in the prior art (example 2).

EXAMPLE 1

Preparation of a catalyst with 5% Pd and 3.5% Bi on carbon by depositing bismuth onto a palladium on carbon or Pd/C catalyst commercially available.

A quantity of 6 g of dry Pd/C catalyst commercially available (DEGUSSA 198 R/W with 5% Pd) is suspended in 80 ml of distilled water acidified with 1ml of concentrated hydrochloric acid (37% HCl). To this suspension is added a solution constituted by 0.3 g of bismuth subnitrate dissolved in a mixture of 2 ml of concentrated hydrochloric acid and 5 ml of distilled water.

Stirring is maintained for two hours, then 5 g of caustic soda in solution in 30 ml of water and introduced in the mixture. The mixture is brought to a temperature of 40°-50° C. for four hours, then 1.5 ml of formalin (37-38% aqueous solution) is added. The mixture is brought to a temperature of 85° C. for 1 hour. The catalyst thus obtained is filtered and washed.

EXAMPLE 2

Preparation of a catalyst with 5 wt % of Pd and 3.5% of Bi on carbon by depositing a bismuth before depositing palladium.

A quantity of 6 g of dry active carbon is suspended in 80 ml of distilled water. To this suspension, A quantity of 6 g of dry active carbon is suspended in 80 ml of distilled water. To this suspension, there is added a solution constituted by 0.3 g of bismuth subnitrate dissolved in a mixture of 3 ml of concentrated hydrochloric acid and of 5 ml of distilled water.

Stirring is maintained for six hours in order to cause the bismuth to completely adsorb on the active carbon.

Then, there is added a solution of 0.5 g of palladium chloride (0.3 g of metal palladium) in 1.5 ml of hydrochloric acid and 5 ml of distilled water. There is added 4 g of caustic NaOH in solution in 30 ml of water and the mixture is brought to a temperature of 40° C. for 5 hours. After adding 1.5 ml of a 37% formalin solution, the suspension is maintained at a temperature of 85° C. for 1 hour. The catalyst thus obtained, is filtered and washed.

In connection with example 3, the stability of the catalyst used according to the invention is compared with the stability of the catalyst used in the prior art.

EXAMPLE 3

A series of experiments of oxidation of glucose is carried out by introducing each time individually into a reaction tank having a capacity of 1 liter, equipped with a stirring device and a thermometer, a sintered rod for air introduction purposes, an electrode and a continuous introduction device, a quantity of 666 g of an aqueous glucose solution with 30% of dry matters (containing 200 g of glucose) as well as a quantity of 6 g of respectively each of the dry catalysts according to examples 1 and 2.

The reaction takes place at 35° C. and air is blown while simultaneously introducing a 30% aqueous sodium hydroxide solution in order to maintain the pH at a value of 8.8±0.3.

The reaction is stopped when the theoretical quantity of NaOH has been consumed, which gives the speed or duration time of the reaction; the reaction product is then filtered out and a determination is made, on the one hand, of the percentage of the product wanted present in the reaction medium, which gives the selectivity of the reaction and, on the other hand, of the percentage of residual reducing sugars.

Recycling is carried out 40 times without intermediate regeneration, that is to say 40 successive experiments are carried out with the catalyst used according to the invention (example 1); recycling is carried out 25 times without regeneration in the case of the catalyst used in the prior art (example 2).

The results recorded in table I are those of respectively the 40 and 25 successive experiments.

TABLE I

| Number of recycling operations | Pd/Bi/C Catalyst (Bi deposited after Pd) Example 1 | | | Pd/Bi/C Catalyst (Bi deposited before Pd) Example 2 | | |
|---|---|---|---|---|---|---|
| | Reaction time (hr) | Reducing sugars (in %) | Gluconate yield (in %) | Reaction time (hr) | Reducing sugars (in %) | Gluconate yield (in %) |
| 1 | 3.20 | 1.3 | 98.5 | 3.25 | 1.1 | 98.3 |
| 5 | 4.20 | 1.0 | 98.5 | 4.10 | 1.0 | 98.8 |
| 10 | 4.00 | 1.2 | 98.6 | 3.45 | 1.2 | 98.7 |
| 15 | 3.20 | 1.1 | 98.4 | 4.55 | 1.8 | 98.0 |
| 20 | 3.30 | 1.4 | 98.4 | 6.20 | 2.3 | 97.0 |
| 25 | 3.45 | 1.4 | 98.2 | 8.00 | 2.9 | 97.4 |
| 30 | 3.25 | 1.5 | 98.3 | | | |
| 35 | 3.40 | 1.9 | 98.0 | | | |
| 40 | 4.00 | 2.1 | 97.6 | | | |

The results recorded in table I show that the catalyst used according to the present invention (example 1) retains an excellent catalytic activity; practically no increase in the reaction time has been observed during the 40 tests and the yield of sodium gluconate as well as the content of reducing sugars remain constant too.

The catalyst used in the prior art (example 2) shows a significant loss of activity after 20 tests, with an increase in the reaction time and in the reducing sugars, so that the reaction time becomes incompatible after 25 tests.

In example 4, there is studied the influence, with the catalyst used according to the invention, of the proportion of bismuth.

EXAMPLE 4

(a) Preparation of a Pd/carbon catalyst.

A quantity of 6 g of active carbon is suspended in 100 ml of distilled water containing 4 g of caustic sodoim hydroxide. To the suspension, there is added 0.5 g of palladium chloride (0.3 g of palladium expressed in terms of metal) solubilized in 5 ml of distilled water to which there is added 1.5 ml of concentrated hydrochloric acid. The palladium is caused to be adsorbed for 4 hours at 40°–50° C.; then, there is added 1.5 ml of formalin (37% aqueous solution) and the temperature is raised to 85° C. for 1 hour.

The filtered catalyst is washed before depositing the promoter.

(b) Deposit of decreasing quantities of promoter (bismuth)

The deposit of bismuth onto the Pd/C catalyst prepared as indicated above is carried out in the same way as in example 1. There are successively used solutions of bismuth subnitrate respectively containing 0.6 g, 0.3 g, 0.15 g, 0.080 g, 0.040 g, which results in as many catalysts containing respectively 140 %, 70 %, 35 %, 19 % and 9 % of bismuth expressed in terms of metal with respect to the palladium expressed in terms of metal.

The same operating procedure as described in example 3 is used in order to oxidize the glucose into gluconic acid.

In table II, there are combined :
the reaction time,
the proportion of reducing sugars within the product obtained,
the proportion of Na-gluconate and
the proportion of glucaric acid which is present for the reactions obtained with, on the one hand, the five catalysts just mentioned, the bismuth concentration, and, on the other hand, with the Pd catalyst on active carbon without promoter (control).

TABLE II

| Bismuth content with respect to palladium (%) | Reaction time | Reducing sugars | Glucaric acid | Sodium gluconate |
|---|---|---|---|---|
| 140 | 4.20 hr | 1.4 | 0.8 | 98.2 |
| 70 | 3.10 hr | 1.3 | 1.0 | 97.7 |
| 35 | 3.10 hr | 1.2 | 1.2 | 97.8 |
| 19 | 2.40 hr | 1.8 | 1.3 | 97.6 |
| 9 | 4.10 hr | 2.6 | 1.7 | 96.5 |
| 0 (control) | 5.20 hr | 7.2 | 2.1 | 93.8 |

The results obtained show that the bismuth content has but a limited influence on the speed and selectivity of the reaction.

In example 5, there is studied the influence of the use of Pb and antimony as promoter.

EXAMPLE 5

(a) Preparation of the catalyst containing lead as promoter.

This is a catalyst with 5% of Pd and 2.5% of Pb on carbon with deposit of lead onto a Pd/C catalyst commercially available.

A quantity of 6 g of dry Pd/C catalyst commercially available (DEGUSSA 198 R/W with 5% Pd) is suspended in 80 ml of distilled water. To this suspension, there are added 20 ml of an aqueous solution containing 0.3 g of lead acetate. The lead is left to be adsorbed for 1 hour under stirring. There is added 30 ml of an aqueous solution containing 4 g of $Na_2CO_3$ and the mixture obtained is brought to a temperature of 40° C. for 4 hours. There is added 1.5 ml of formalin and the suspension is maintained at 85° C. for 1 hour. The catalyst thus obtained is then filtered and washed with distilled water.

(b) Preparation of the catalyst containing antimony as promoter.

This is a catalyst with 5% of Pd and 1% of Sb on carbon with deposit of antimony onto a Pd/C catalyst commercially available.

A quantity of 6 g of dry Pd/C catalyst commercially available (DEGUSSA 198 R/W with 5 % Pd) is suspended in 80 ml of distilled water. To the suspension there is added an aqueous solution constituted by 0,1 g of $SbCl_3$, 2 ml of concentrated HCl and 5 ml of distilled water. Stirring is maintained for 3 hours and there are added 50 ml of an aqueous solution containing 8 g of $Na_2CO_3$, then dropwise 10 ml of a 0.1 N sodium hydroxide solution containing 0.2 g of Na-boron hydride. The mixture obtained is brought to a temperature of 85° C. for 1 hour. The catalyst thus obtained is then filtered and washed with distilled water.

(c) The operating procedure of Example 3 is used in order to oxidize glucose into sodium gluconate, whereby utilizing the two aforesaid doped catalysts and the catalyst based only on palladium (control).

The results are recorded in table III.

TABLE III

| Catalyst used | Reaction time | Reducing sugars (in %) | Gluconate yield (in %) |
|---|---|---|---|
| 5% Pd – 2.5% Pb | 2.10 hr | 3.0 | 96.0 |
| 5% Pd – 1.0% Sb | 2.40 hr | 3.1 | 96.1 |
| 5% Pd (control) | 5.20 hr | 7.2 | 93.8 |

These results show that the promoters used considerably increase the kinetic and the selectivity of the reaction.

In the following Example 6, the process according to this invention is carried out for the oxidation of glucose and of three aldoses other than glucose.

The catalyst used is the one of example 1.

The operating procedure is the one of example 3, the glucose being successively replaced with :

D (+) mannose
D (−) arabinose
D (−) ribose.

The reaction time and the corresponding aldonic acid yield are recorded in table IV.

TABLE IV

| Nature of aldose | Reaction time | Yield in corresponding aldonic acid (in %) |
|---|---|---|
| D(+) glucose | 3.20 hr | 98.0 |
| D(+) mannose | 2.30 hr | 95.7 |
| D(−) arabinose | 2.40 hr | 98.8 |
| D(−) ribose | 2.00 hr | 96.9 |

The results obtained are comparable to the ones obtained with the glucose.

We claim:

1. In a process for the oxidation of an aldose into the corresponding aldonic acid with an oxygen-containing gas in an aqueous alkaline reaction medium in the presence of a promoted palladium-based catalyst which has been prepared by depositing on an inert support a palladium compound, then adding a promoter compound selected from the group consisting of the metals of groups IV, V and VI of the periodic system, reducing the promoted palladium-based compound and using the thus obtained catalyst as such in said oxidation.

2. Process according to claim 2, wherein the aldose is glucose.

3. Process according to claim 1, wherein the promoter is selected from the group consisting of bismuth, lead, antimony, tin or selenium.

4. Process according to claim 1, wherein the inert support is selected from the group consisting of finely divided carbon, alumina, silica, silica-alumina, barium sulfate and titanium oxide.

5. Process according to claim 1, wherein the palladium content of the catalyst, expressed in terms of metal, is between 1 and 10 wt % with respect to the inert support.

6. Process according to claim 1, wherein the promoter content of the catalyst, expressed in terms of metal, is between 1 and 300 % with respect to palladium.

7. Process according to claim 1, wherein the promoter content of the catalyst, expressed in terms of metal, is between 5 and 100 wt % with respect to palladium.

8. Process according to claim 1, wherein the aldose is selected from the group consisting of erythrose, threose, ribose, arabinose, xylose, lyxose, allose, altrose, gulose, mannose, idose, galactose, talose.

9. Process according to claim 1, wherein the aldose is in an aqueous solution having a concentration between 5 and 60 wt%.

10. Process according to claim 2, wherein the aldose is a glucose solution having a concentration between 20 and 40 wt %.

11. Process according to claim 1, wherein the catalyst is dispersed in the solution of aldose in a quantity such that the palladium concentration, expressed in terms of metal, is between 0.005 and 1 wt % with respect to the aldose.

12. Process according to claim 1, wherein the catalyst is dispersed in the solution of aldose in a quantity such that the palladium concentration, expressed in terms of metal, is between 0.01 and 0.4 wt % with respect to the aldose.

13. Process according to claim 1, wherein the reaction temperature ranges between 20° and 90° C. for a reaction time comprised between 30 minutes and 5 hours.

14. Process according to claim 1, wherein the reaction temperature ranges between 25° and 60° C. for a reaction time comprised between 30 minutes and 5 hours.

15. Process according to claim 1, wherein the pH of the reaction medium is maintained by means of one or several alkaline agents between 7.5 and 11.0.

16. Process according to claim 1, wherein the pH of the reaction medium is maintained by means of one or several alkaline agents between 8.0 and 10.0.

17. A process according to claim 1, wherein the reaction medium comprises an alkaline agent selected from the group consisting of calcium hydroxide, lithium hydroxide, magnesium hydroxide, zinc or manganese carbonates, or any other zinc or manganese salts for which the corresponding hydroxides are obtained in situ by adding an alkaline agent such as sodium hydroxide or potassium hydroxide.

* * * * *